United States Patent [19]
Augustine

[11] Patent Number: 5,964,792
[45] Date of Patent: *Oct. 12, 1999

[54] CONVERTIBLE THERMAL BLANKET

[75] Inventor: Scott D. Augustine, Bloomington, Minn.

[73] Assignee: Augustine Medical, Inc., Eden Prairie, Minn.

[*] Notice: This patent is subject to a terminal disclaimer.

[21] Appl. No.: 08/965,306

[22] Filed: Nov. 6, 1997

Related U.S. Application Data

[63] Continuation of application No. 08/691,593, Aug. 2, 1996, Pat. No. 5,733,318.

[51] Int. Cl.$^6$ ....................................................... A61F 7/00
[52] U.S. Cl. ......................... 607/104; 607/108; 607/114
[58] Field of Search ..................... 607/104, 96, 108–112, 607/107, 114; 165/46; 126/204; 219/212

[56] References Cited

U.S. PATENT DOCUMENTS

| | | |
|---|---|---|
| 222,690 | 12/1879 | Goldschmidt . |
| 1,399,095 | 12/1921 | Webb, Sr. . |
| 1,777,982 | 10/1930 | Popp . |
| 2,093,834 | 9/1937 | Gaugler .................................... 128/145 |
| 2,110,022 | 3/1938 | Kliesrath ....................................... 5/334 |
| 2,122,964 | 7/1938 | Sweetland ................................... 34/26 |
| 2,512,559 | 6/1950 | Williams ....................................... 5/347 |
| 2,601,189 | 6/1952 | Wales, Jr. .................................... 4/160 |
| 2,706,988 | 4/1955 | Weber ..................................... 128/402 |
| 3,243,827 | 4/1966 | Kintner ......................................... 5/334 |
| 3,418,726 | 12/1968 | Sparks ........................................ 34/99 |
| 3,610,251 | 10/1971 | Sanderson ............................... 128/379 |
| 3,610,323 | 10/1971 | Troyer ....................................... 165/46 |
| 3,691,646 | 9/1972 | Ruffolo ....................................... 34/90 |
| 3,714,947 | 2/1973 | Haddy ..................................... 128/400 |
| 3,757,366 | 9/1973 | Sacher ......................................... 5/347 |
| 4,572,188 | 2/1986 | Augustine et al. ...................... 128/380 |
| 4,660,388 | 4/1987 | Greene, Jr. ............................... 62/261 |
| 4,777,802 | 10/1988 | Feher ........................................... 62/3 |
| 4,807,644 | 2/1989 | Sandhaus ................................. 128/849 |
| 4,867,230 | 9/1989 | Voss ........................................ 165/46 |
| 5,125,238 | 6/1992 | Ragan et al. .......................... 62/259.3 |

(List continued on next page.)

FOREIGN PATENT DOCUMENTS

| | | |
|---|---|---|
| 0 311 336 | 8/1988 | European Pat. Off. . |
| 33 08 553 | 3/1983 | Germany . |
| 0 113 420 | 11/1983 | Germany . |
| 716746 | 10/1954 | United Kingdom . |
| 1 334 935 | 3/1971 | United Kingdom . |
| 1 461 383 | 4/1973 | United Kingdom . |
| 1 532 219 | 6/1975 | United Kingdom . |
| 1 566 207 | 5/1977 | United Kingdom . |
| WO 85/03216 | 8/1985 | WIPO . |

OTHER PUBLICATIONS

Webster's Ninth New Collegiate Dictionary definition of "laminate".

Webster's Third New International Dictionary, p. 250, definition of "bond".

McGraw–Hill Encyclopedia of Science & Technology, 7th Ed., p. 713, definition of "bonding".

"Normothermia in the OR" Augustine Medical, Inc., Oct. 1989.

*Primary Examiner*—Cary O'Connor
*Assistant Examiner*—Ryan Carter
*Attorney, Agent, or Firm*—Gray Cary Ware Freidenrich

[57] ABSTRACT

One or more portions of an inflatable thermal blanket that is sized sufficiently to fully cover a patient are gathered and maintained in a non-inflated condition by a closure such that a thermally-controlled inflating medium admitted into the blanket is prevented from being admitted into the gathered portion(s), thereby leaving a primary part of the patient covered and exposing a part of the patient for medical attention. Thereafter the closure can be released to permit the inflating medium to be admitted into the gathered portion such that the gathered portion self-erects and assumes an inflated condition. The released thermal blanket covers the entire patient and bathes the patient in the inflating medium. The closure can be provided as an elongated tape strip with a central perforation that can be separated.

22 Claims, 14 Drawing Sheets

U.S. PATENT DOCUMENTS

| | | | |
|---|---|---|---|
| 5,184,612 | 2/1993 | Augustine | 128/400 |
| 5,300,100 | 4/1994 | Hickle et al. | 607/107 |
| 5,300,101 | 4/1994 | Augustine et al. | 607/107 |
| 5,300,102 | 4/1994 | Augustine et al. | 607/107 |
| 5,324,320 | 6/1994 | Augustine et al. | 607/107 |
| 5,336,250 | 8/1994 | Augustine | 607/107 |
| 5,343,579 | 9/1994 | Dickerhoff et al. | 5/421 |
| 5,350,417 | 9/1994 | Augustine | 607/104 |
| 5,360,439 | 11/1994 | Dickerhoff et al. | 607/104 |
| 5,383,918 | 1/1995 | Panetta | 607/104 |
| 5,384,924 | 1/1995 | Dickerhoff et al. | 5/421 |
| 5,405,370 | 4/1995 | Irani | 607/107 |
| 5,405,371 | 4/1995 | Augustine et al. | 607/107 |
| 5,443,488 | 8/1995 | Namenye et al. | 607/104 |
| 5,514,169 | 5/1996 | Dickerhoff et al. | 607/107 |
| 5,545,194 | 8/1996 | Augustine | 607/104 X |
| 5,620,482 | 4/1997 | Augustine et al. | 607/107 | ns sheet
CONVERTIBLE THERMAL BLANKET

This application is a continuation of application Ser. No. 08/691,593, filed Aug. 2, 1996, now U.S. Pat. No. 5,733,318.

BACKGROUND OF THE INVENTION

1. Field of the Invention

This invention relates generally to thermal blankets and, more particularly, to thermal blankets that deliver a bath of a thermally-controlled medium to a body.

2. Description of the Related Art

It often is necessary to bathe a patient in a thermally-controlled medium for the purpose of controlling the patient's body temperature. For example, it is important to keep a patient warm during surgery and to warm the patient post-operatively to reduce the risk of hypothermia. Typically, a patient's body temperature is controlled during surgery by using operating room blankets that cover the parts of a patient's body not being operated upon. Multiple blankets are overlaid, or variously shaped blankets having cut-outs or flaps are used, to cover most of the patient and still provide access to target surgical sites. After surgery, the patient is covered with a full-body blanket that covers all of the patient except for the head. Thus, as much of the patient as possible is kept covered duriing surgery to keep the patient warm while providing access to the operating site and after surgery a full body blanket keeps the patient warm.

It is known to provide an inflatable covering into which a thermally-controlled inflating medium is introduced. For warming purposes, the inflating medium can be warmed air. The thermally-controlled medium also can be cooled air. When such a covering is inflated, it self-erects about a patient to produce a structure having a thermally-controlled interior environment. See, for example, U.S. Pat. Nos. 4,572,188 and 5,324,320, commonly assigned with this application and incorporated herein by this reference.

The prior art inflatable covering is an inflatable blanket that includes an array of apertures on its underside. The thermally-controlled medium is exhausted from the apertures into the erected structure and bathes the patient in the inflating medium. The temperature of the environment provided by the inflated blanket is determined by the temperature of the inflating medium. Thus, relatively uniform and precise control over the ambient environment of the patient can be achieved. Such thermal blankets are advantageously used to warm or cool patients before, during, and after surgery.

To expose an operating site during surgery or otherwise permit access to part of a patient's body while using an inflatable thermal blanket, a patient is covered with the blanket and a blanket area around the site of interest is sealed to provide a boundary against deflation. The blanket within the sealed area can be cut out, creating an open space in the blanket for access to the site of interest, while maintaining the inflatable integrity of the blanket. The blanket can then be inflated with the thermally-controlled medium to completely cover the patient except for the site of interest and thereby control the patient's temperature during surgery. After surgery, the inflatable blanket can be removed and replaced with a full-body blanket or a supplemental blanket can be draped across the exposed site. See, for example, U.S. patent application Ser. No. 071638,748, commonly assigned with this application and incorporated herein by this reference.

It would be advantageous if it were not necessary to change blankets or add blankets between surgery or other medical procedures and the recovery period. This would permit a single blanket to be used for each patient, rather than multiple blankets. A single blanket would make it unnecessary to layer multiple blankets or to cut or shape blankets to provide surgical access to parts of a patient's body. The cost of maintaining an inventory of blankets and the time spent changing or modifying blankets also could be saved.

From the discussion above, it should be apparent that there is a need for a thermal blanket that can be used to cover a patient during surgery or other medical procedures in which it is necessary to gain access to a portion of the patient's body and that also can be used after the medical procedure is completed to fully cover the patient and provide a thermally-controlled environment. The present invention satisfies this need.

SUMMARY OF THE INVENTION

In accordance with the invention, an inflatable, self-erecting thermal blanket includes one or more portions that are gathered in a non-inflated condition and held there by a closure such that a thermally-controlled inflating medium that is admitted into the blanket is prevented from being admitted into the gathered portion(s), thereby inflating a primary part of the blanket, which can be used to cover a patient, and leaving a void in the area covered by the blanket so as to expose an area of the patient's body for medical treatment. After the medical treatment, the closure can be released, thereby permitting the inflating medium to be admitted into the gathered portion such that the gathered portion inflates and covers the exposed area of the patient's body. The released thermal blanket then covers the entire patient and bathes the patient in the inflating medium. In this way, a single thermal blanket can be used to provide a thermally controlled environment and expose an area of a patient during treatment and also can be converted to fully cover the patient after treatment.

In one aspect of the invention, the gathered portion of the thermal blanket is created by rolling or folding an extension of the blanket onto itself and is maintained in the gathered condition adjacent the primary portion of the blanket by a closure comprising an elongated strip of tape that bridges both the gathered portion and the primary portion. The strip is provided with a release element that permits the gathered portion of the strip to be separated from the primary portion of the strip. When a patient is to be fully covered, the release element releases the gathered portion, which is then inflated by the inflating medium and covers a previously exposed area of the patient.

The closure and the release element can be provided by a variety of structures. For example, in one aspect of the invention, the closure comprises a strip that includes two longitudinal edges, one of which is attached to the gathered portion and the other of which is attached to the primary portion of the thermal blanket. The strip can include a central perforation that can be split open such that the gathered portion edge of the strip can be separated from the primary portion edge of the strip, releasing the gathered portion of the thermal blanket and permitting it to be unfurled and inflated. Alternatively, the release element can comprise a tear string embedded in a strip that bridges the gathered portion and primary portion. When the patient is to be fully covered, the tear string can be pulled out of the strip to separate the two edges of the strip and release the gathered portion. In another aspect of the invention, the release element can comprise a releasable hook and loop system having a hook strip attached to either the gathered portion or the primary portion and a loop strip attached to the other portion. The hook strip can be easily separated from the loop strip. A variety of other closures and release elements will occur to those skilled in the art.

Other features and advantages of the present invention should be apparent from the following description of the preferred embodiments, which illustrate, by way of example. the principles of the invention.

DESCRIPTION OF THE PREFERRED EMBODIMENTS

Figure 1:
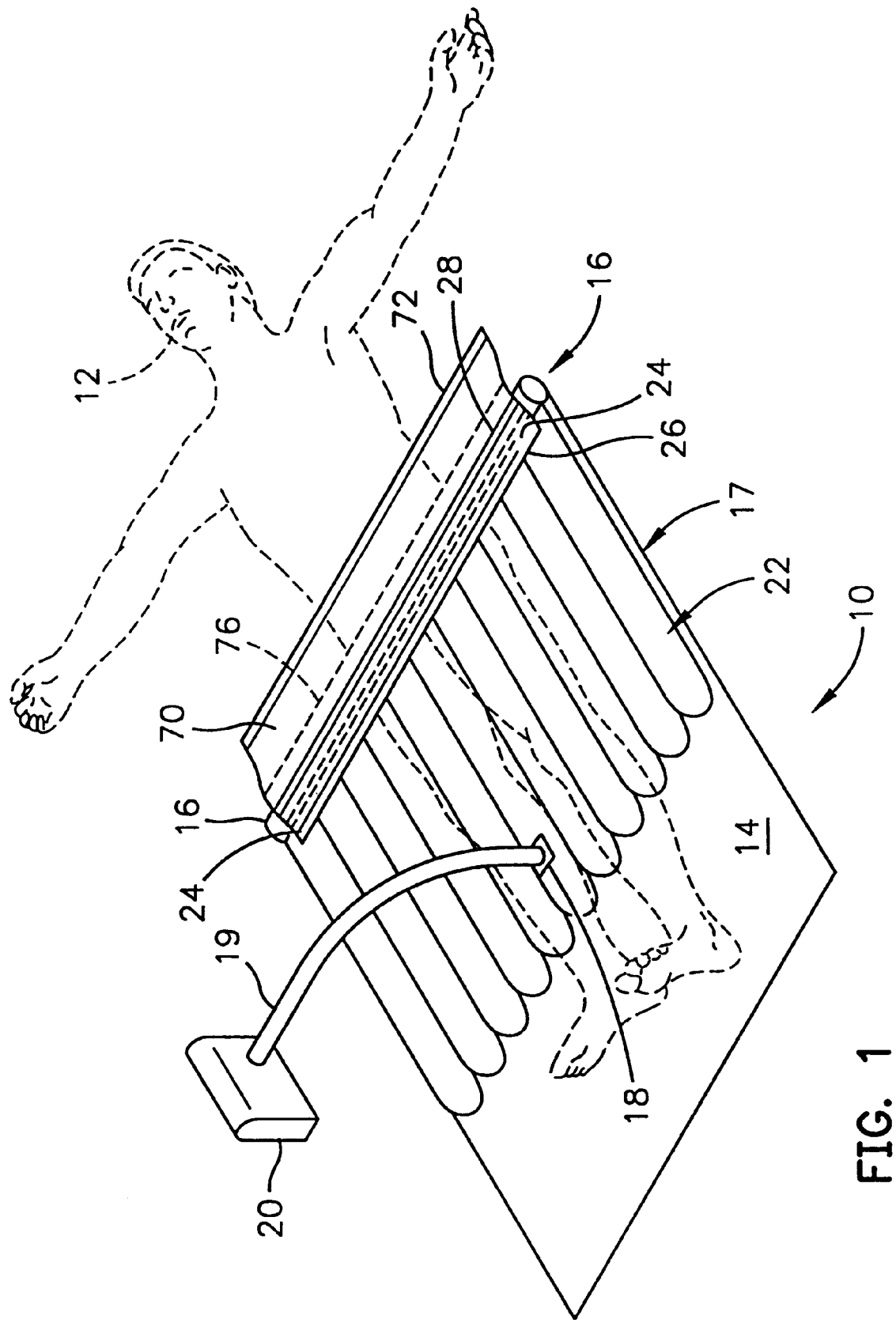
FIG. 1 is a view of an inflatable thermal blanket constructed in accordance with the present invention to initially cover a patient's lower body, having a gathered portion of the blanket in a non-inflated condition to permit access to the patient's upper body during medical treatment.

FIG. 1 shows an inflatable thermal blanket 10 constructed in accordance with the present invention. As shown, the blanket provides access to the upper body of a patient 12 during medical treatment and includes a lower end 14 that is placed near the feet of the patient and an upper end rolled onto itself to form a gathered portion 16 and a primary portion 17. Thus, the torso of the patient 12 is not covered by the blanket in the gathered condition. An inlet port 18 of the blanket is connected by a hose 19 to a heater/blower assembly 20 that produces a thermally controlled inflating medium, such as heat and air. When the blanket 10 is inflated with the heater/blower assembly, the blanket erects itself into a structure having a quilted upper surface 22. Medical treatment can then be provided to the exposed torso of the patient while the remainder of the patient's body is kept warm by the blanket. A closure 24 maintains the gathered portion 16 in a non-inflated condition. After the medical treatment has been completed, the closure is opened so as to release the gathered portion, permitting the inflating medium to enter the gathered portion, inflating it so that it assumes the configuration illustrated in FIG. 2. In this way, the same blanket can be used to keep an area of the patient's body warm during medical treatment and then can be converted into a full body covering after completion of treatment.

Figure 3:
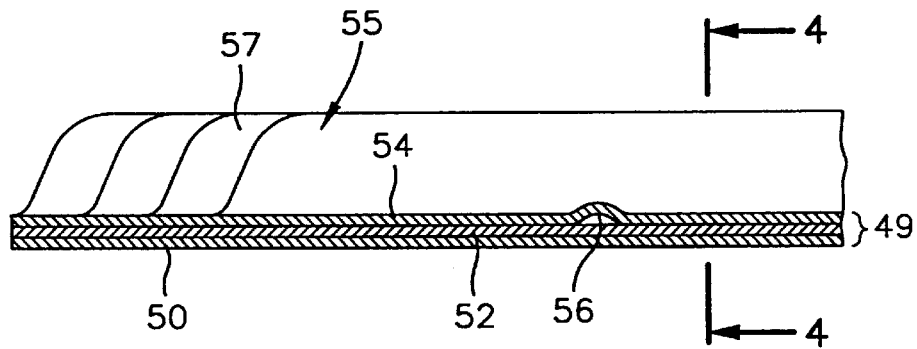
FIG. 3 and FIG. 4 are views illustrating construction details of the blanket illustrated in FIGS. 1 and 2.
Figure 4:
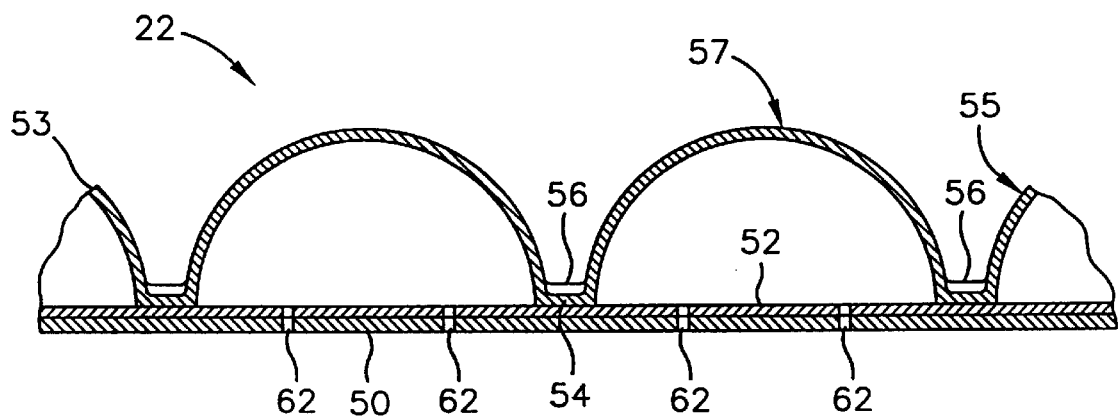

FIG. 3 and FIG. 4 illustrate some of the construction details of the thermal blanket 10. A lower sheet 49 of the blanket is formed by bonding a layer 50 of flexible material to a layer 52 of heat-sealable plastic. In the preferred embodiment, the layers 50 and 52 respectively comprise a layer of non-woven polyester pre-laminated with a layer of heat sealable plastic such as a polypropylene extrusion. An upper layer 53 of the thermal blanket consists of a layer of extruded polypropylene film bonded to the plastic underside layer 52 by a heat-sealing process to form interrupted seams, one of which is indicated by the arrow 54, and inflatable tubes, one of which is indicated by the arrow 55. As can be seen in FIG. 4, the seam 54 forms a passageway 56 between two adjacent tubes 55 and 57.

The thermal blanket 10 bathes a patient in the thermally controlled inflating medium by means of a plurality of apertures 62 illustrated in FIG. 4. The apertures extend through the blanket underside, which includes the layers 50 and 52. The apertures 62 are provided in a pattern determined to produce a uniform flow of the inflating medium from the underside of the blanket. For example, the apertures are provided in a density that varies inversely with the distance of the aperture to the center tube having the inlet port 18. Thus, the ambient temperature beneath the inflated blanket is substantially uniform from edge to edge.

Figure 5:
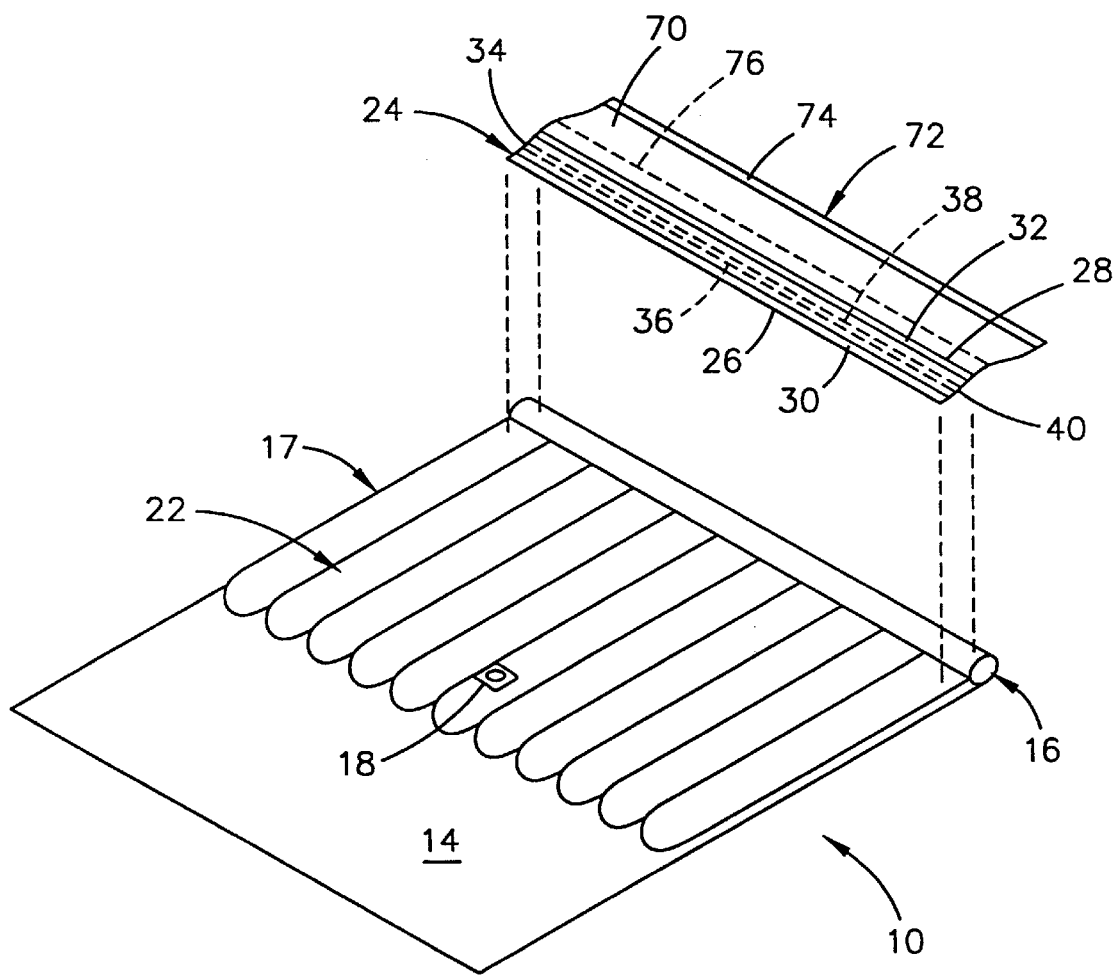
FIG. 5 is an exploded view of the blanket illustrated in FIG. 1 showing the closure before attachment to the blanket.

FIG. 5 illustrates the manner of attaching the closure 24 to the blanket in the gathered position. As illustrated in FIG. 5, the closure comprises an elongated strip having a first edge 26 that is attached to the primary portion 17 of the thermal blanket and a second edge 28 attached to the gathered portion 16 of the blanket. In FIG. 5, the closure 24 is shown in phantom, and therefore a strip of adhesive backing 30 applied along the underside of the first edge is indicated by shading, as is another strip of adhesive backing 32 applied along the underside of the second edge. Thus, the elongated strip of the closure 24 bridges the primary portion 17 and the gathered portion 16, thereby holding the gathered portion 16 in the rolled, non-inflated condition. In this way, when the inflating medium is admitted into the thermal blanket to inflate the primary portion 17 through the inlet 18, the gathered portion does not inflate.

FIG. 5 also shows that a central tear strip 34 is defined between the first edge 26 and second edge 28 of the closure 24 by two parallel perforations 36, 38 that extend along the length of the closure strip. It should be apparent that one end 40 of the tear strip can be grasped and pulled, tearing the perforations apart, thereby releasing the first edge from the second edge, permitting the gathered portion to be unfurled, and permitting the inflating medium to be admitted into the gathered portion to inflate the blanket and assume the condition illustrated in FIG. 2.

The FIG. 5 embodiment shows that the closure 24 also can include an attachment flap 70 that extends outwardly from the second edge 28 of the closure. A free edge 72 of the attachment flap is provided with a strip of adhesive 74 on its underside along its length. The adhesive is used to attach the flap to the patient's body, thereby holding the gathered portion 16 in a fixed relative location. Holding the gathered portion fixed assists the attending medical personnel in maintaining the thermal blanket 10 in a desired location while medical treatment is provided. The attachment flap 70 preferably also includes a perforation 76 that can be torn, thereby releasing the closure 24 (and also the gathered portion 16) from the attachment flap. Thus, the attachment flap can be released independently of, or along with, the elongated strip of the closure 24.

Figure 2:
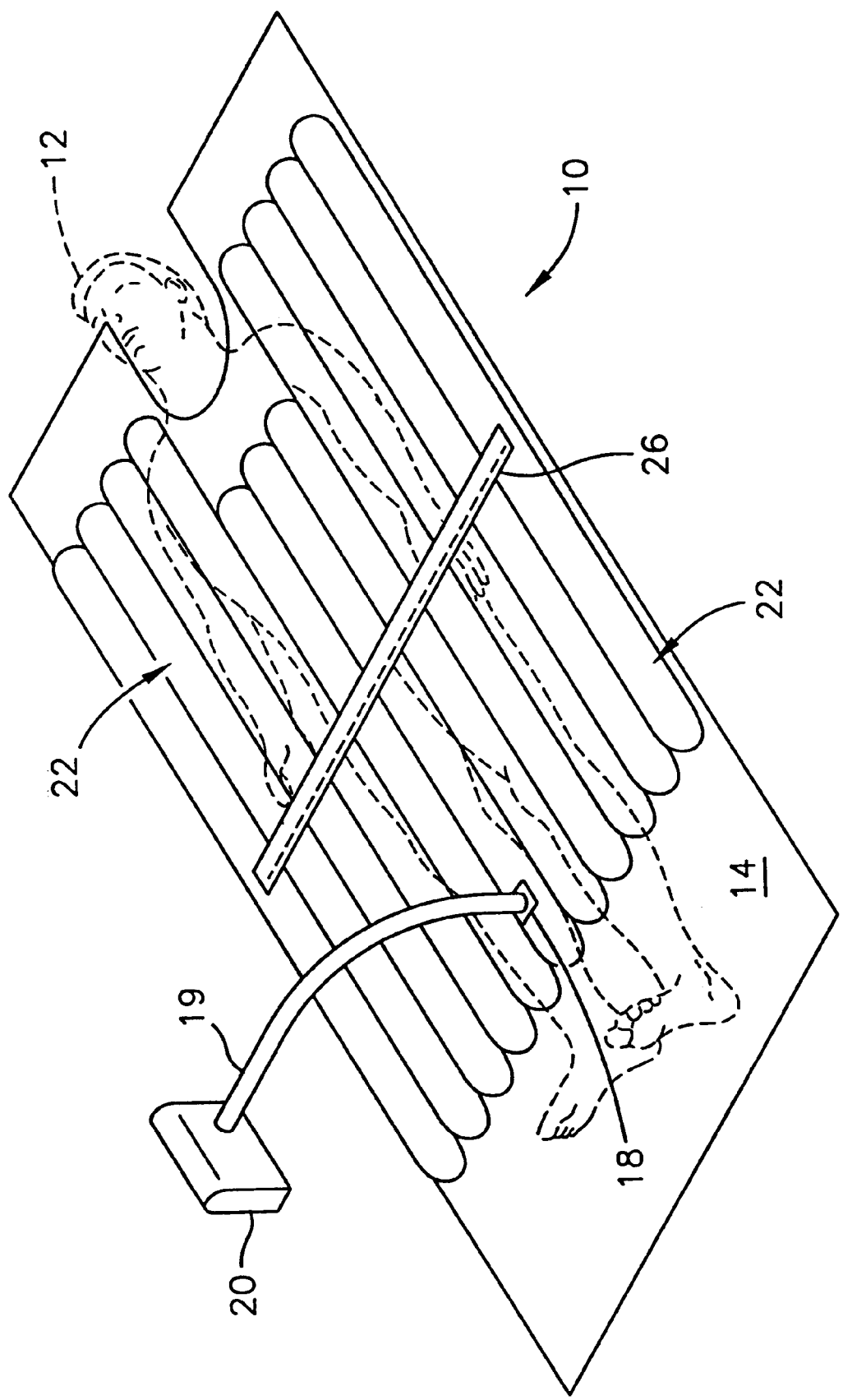
FIG. 2 is a view of the blanket illustrated in FIG. 1 after the gathered portion has been released and the patient fully covered.
Figure 6:
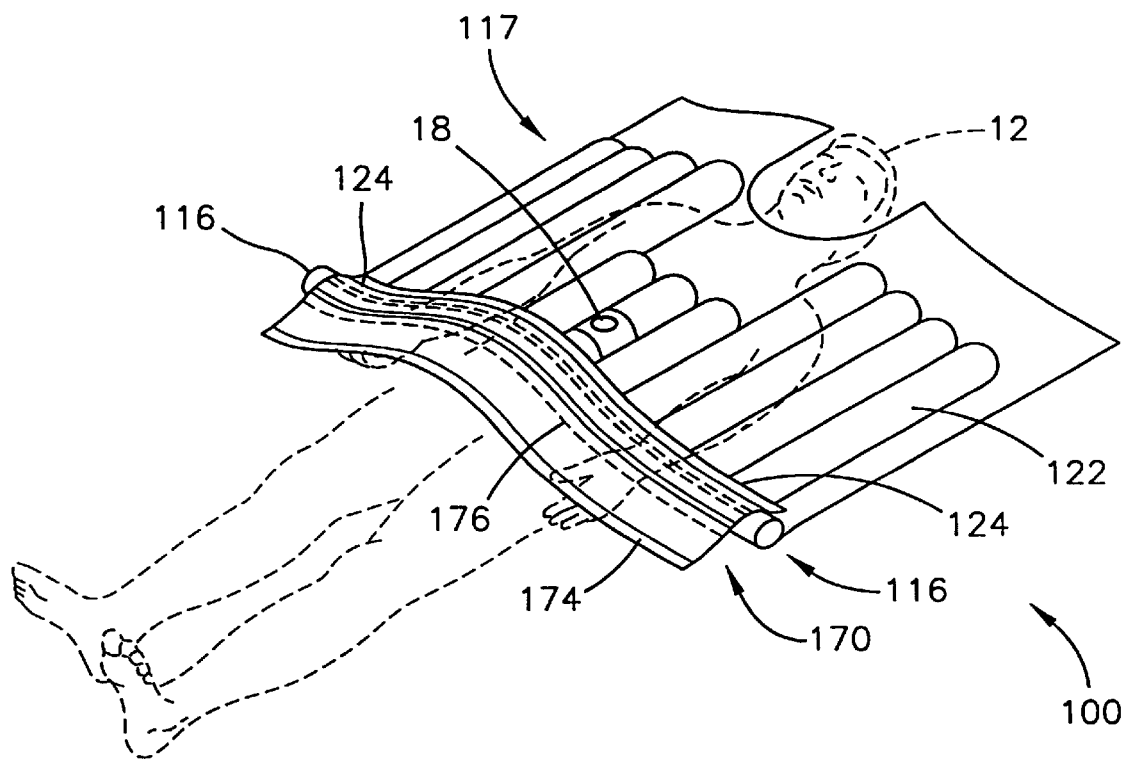
FIG. 6 and FIG. 7 are views of an inflatable thermal blanket constructed in accordance with the present invention to provide access to a patient's lower body during medical treatment.
Figure 7:
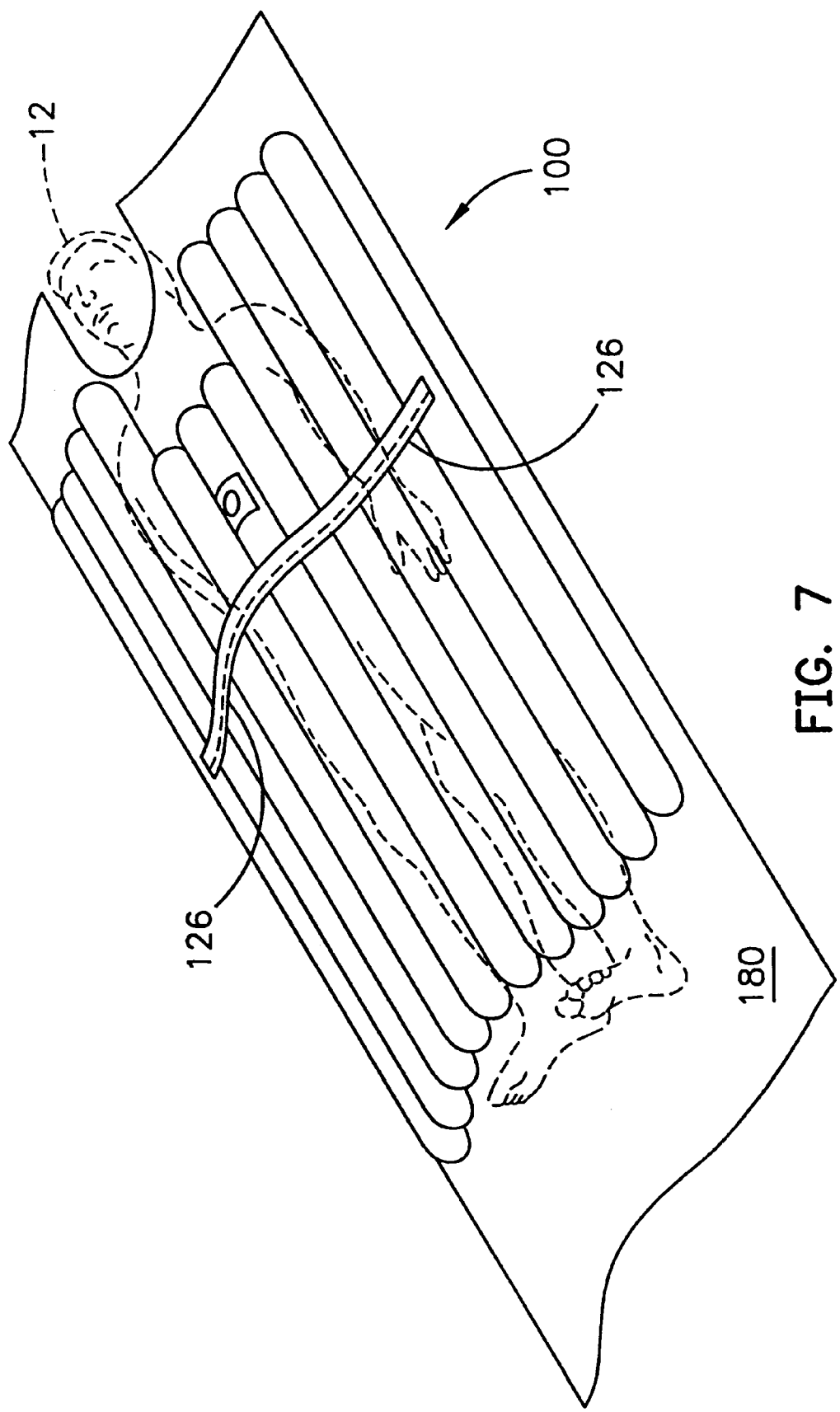

A thermal blanket in accordance with the present invention can be provided in a variety of configurations in addition to that illustrated in FIGS. 1 and 2. For example, FIG. 6 and FIG. 7 illustrate a thermal blanket 100 that provides access to the lower extremities of the patient 12 while covering the torso of the patient during treatment. In FIG. 6 and the remaining drawings, the heater/blower assembly 20 and connected hose 19 are not shown for clarity of illustration, but it should be understood that these elements are included in any actual usage of the thermal blanket. FIG. 6 illustrates the blanket 100 in the gathered condition and FIG. 7 illustrates the blanket in the fully deployed condition. Again, a gathered portion 116 and a primary portion 117 are provided by rolling one end of the thermal blanket onto itself while in a non-inflated condition and maintaining it in the non-inflated condition with a closure 124. As before, an attachment flap 170 can be provided, if desired, with an adhesive strip backing 174 for attaching the gathered portion to the body of the patient. When deployed, the unfurled gathered portion ends in a lower edge 180 at the feet of the patient 12. The primary edge 126 of the released closure remains attached to the surface 122 of the blanket, as illustrated in FIG. 7.

Figure 8:
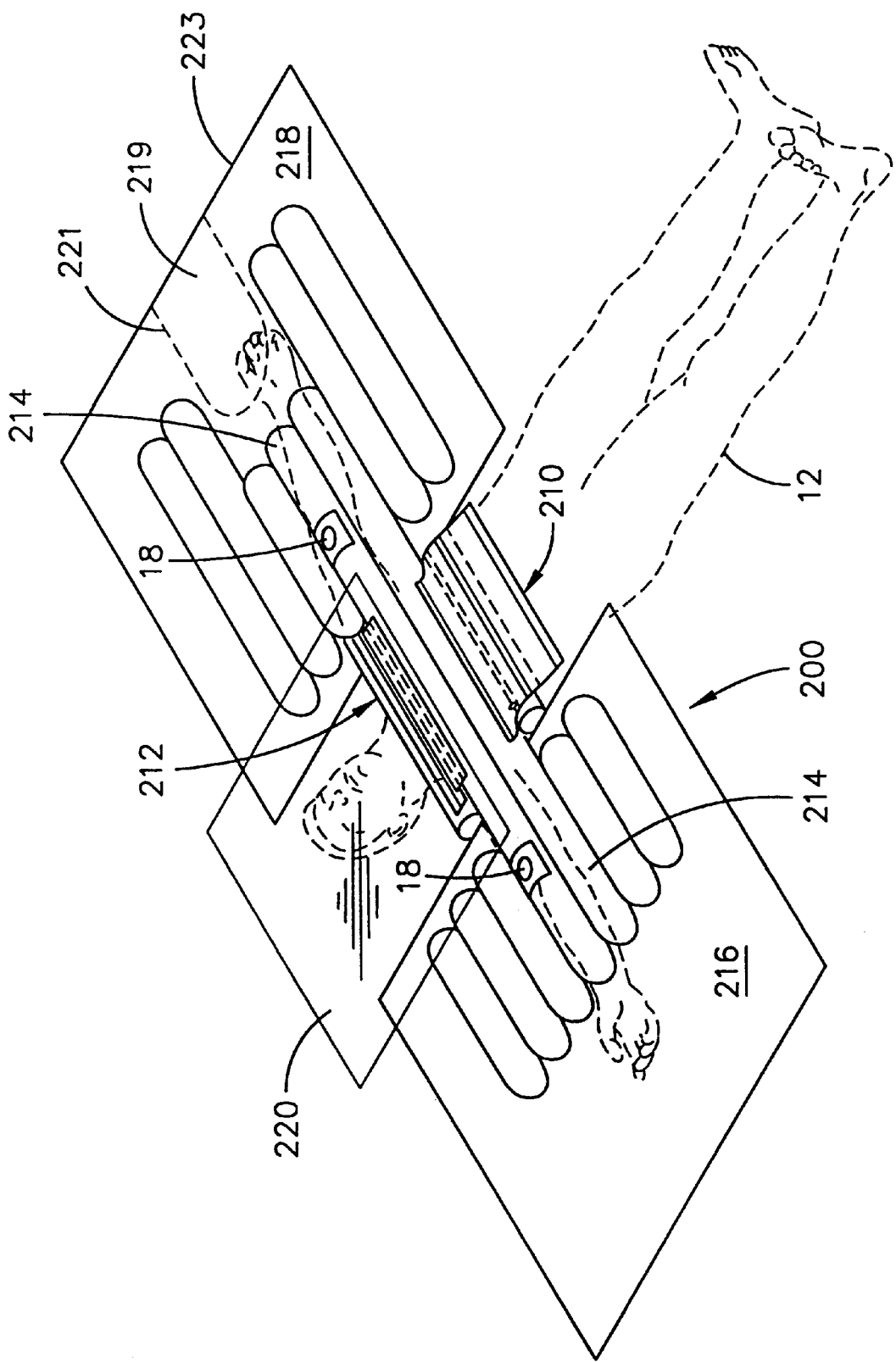
FIG. 8 and FIG. 9 are views of another inflatable thermal blanket constructed in accordance with the present invention to provide access to a patient's lower body during medical treatment.
Figure 9:
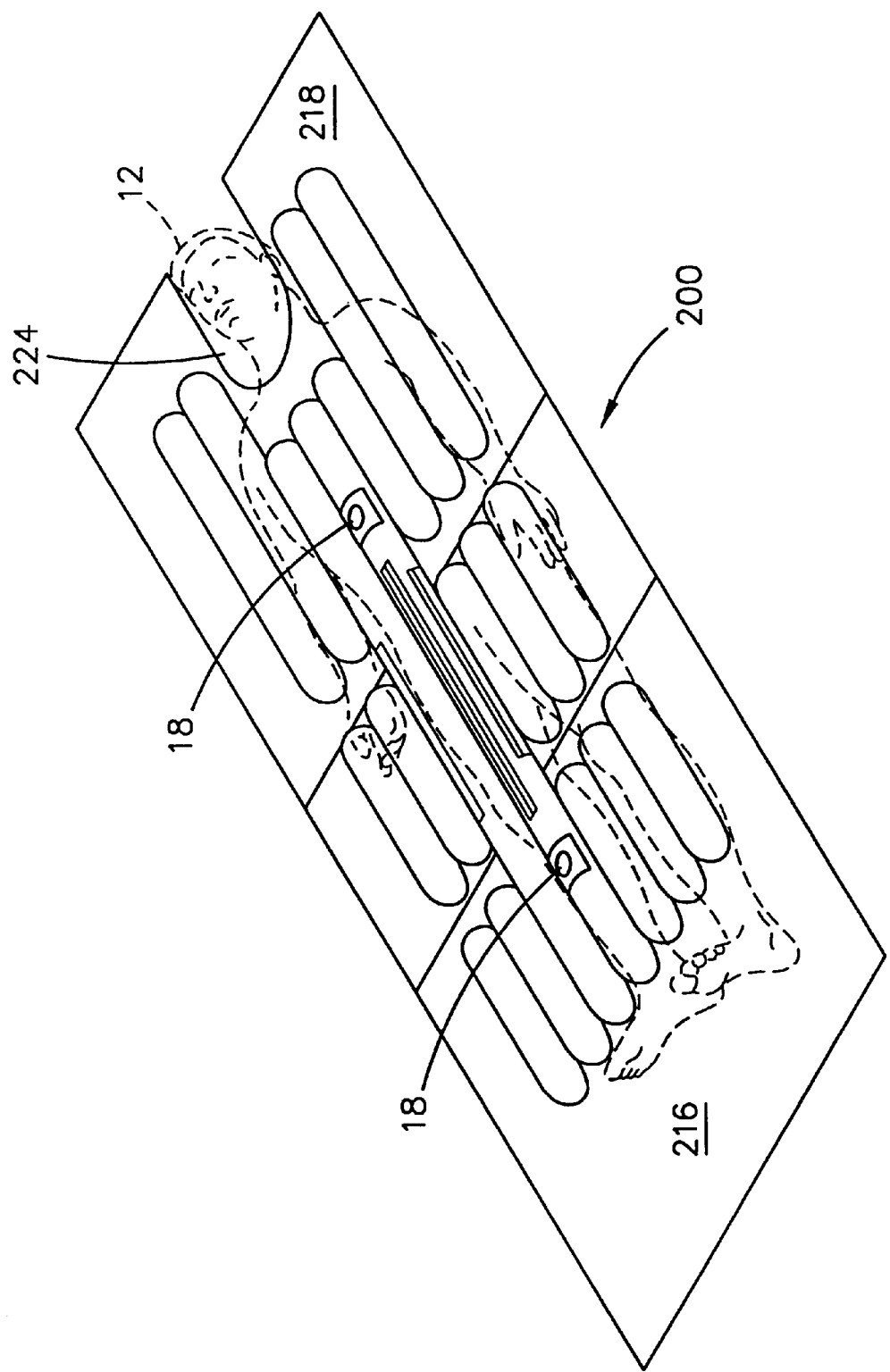

FIGS. 8 and 9 illustrate an alternative embodiment of a blanket 200 for providing access to the lower extremities of the patient. FIG. 8 shows that the blanket can be draped over a patient so that the longest dimension of the blanket extends across the body of the patient from arm to arm. Two gathered portions 210, 212 define a central area 214 of the blanket, which covers the torso of the patient and bridges a blanket lower end 216 and a blanket upper end 218. The lower end and upper end are each provided with an inlet port 18 but communicate internally so that both ends are simultaneously inflated even if only one port is connected to an inflating medium. An optional head drape 220 can be provided to maintain the temperature of the patient's head. The blanket 200 also includes, in its upper end 218, a removeable section 219 defined by a U-shaped perforation 221. The removeable section 219 can be removed by tearing along the perforation 221 to leave a U-shaped indentation in the upper end edge 223. The indentation is indicated at 224 in FIG. 9. FIG. 9 shows the blanket 200 after medical care has been provided and the gathered portions have been released. As can be seen in FIG. 9, after the gathered portions are released, the blanket 200 is preferably rotated so that the longest dimension of the blanket is oriented over the length of the patient's body with the patient's head received in the U-shaped indentation 224. Thus, complete coverage of the patient is obtained.

Figure 10:
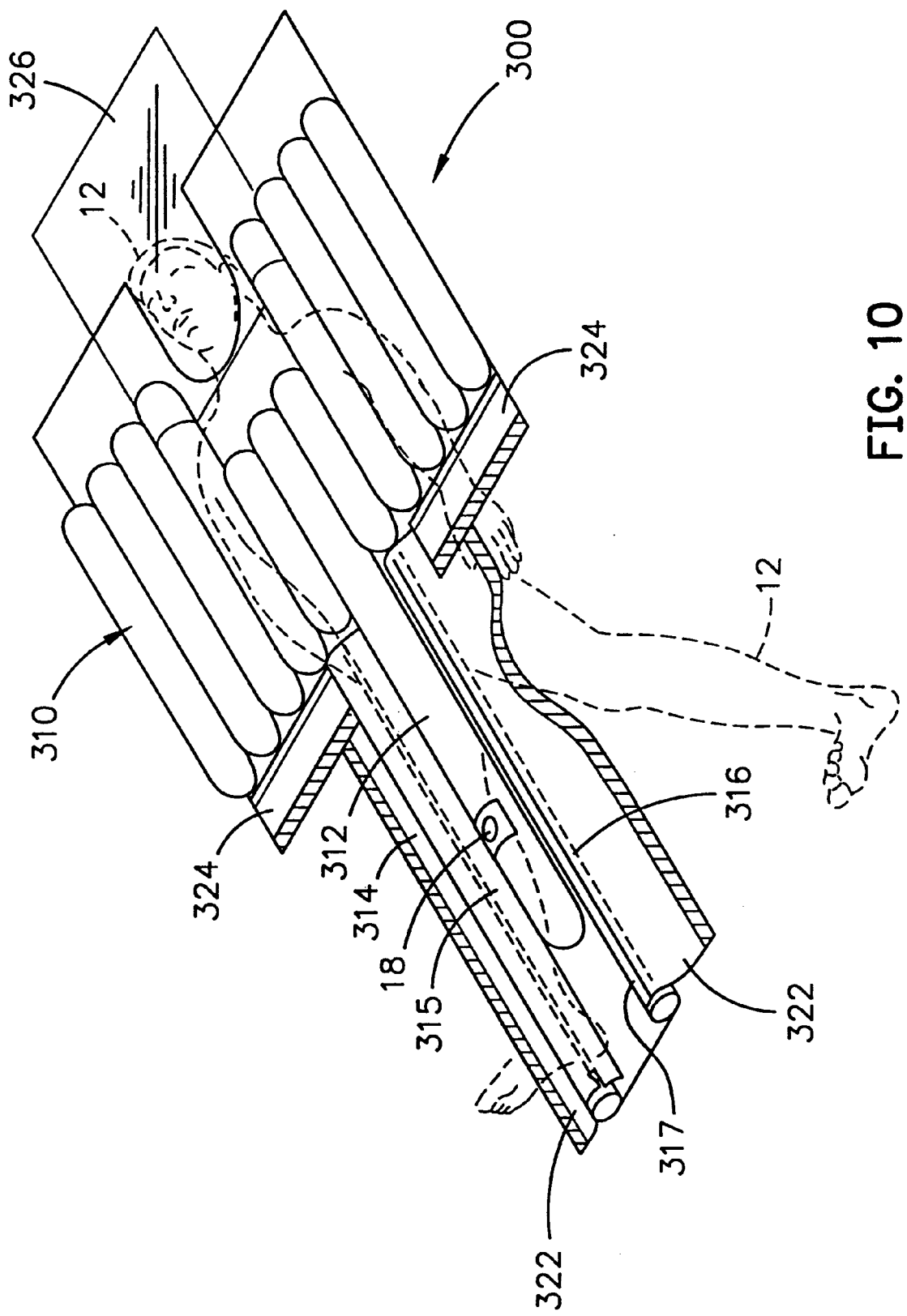
FIG. 10, FIG. 11, and FIG. 12 are views of a third inflatable thermal blanket constructed in accordance with the present invention to provide access to a patient's lower body during medical treatment.
Figure 11:
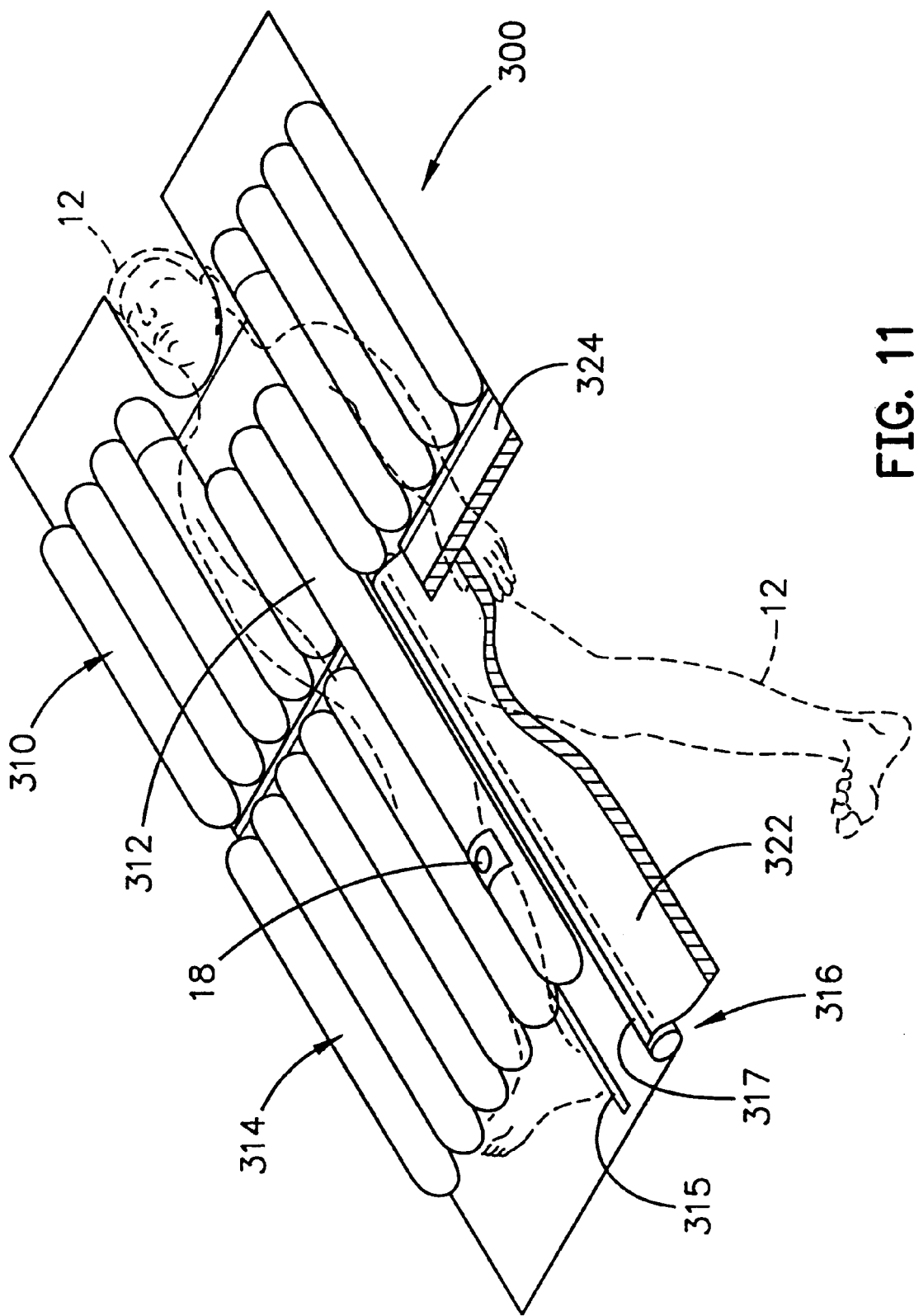
Figure 12:
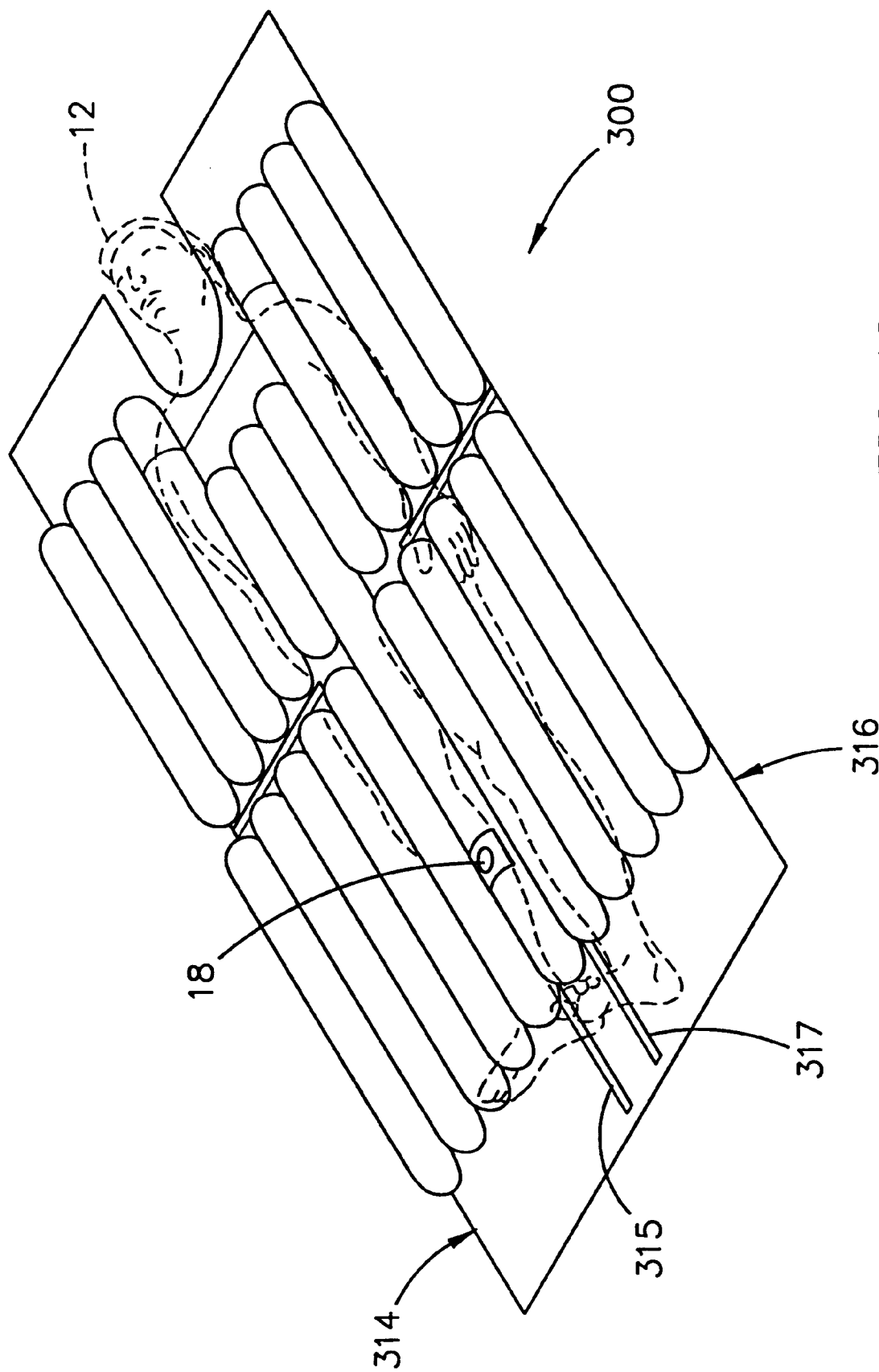

FIGS. 10–12 illustrate an embodiment 300 of the thermal blanket in which access is provided to the lower extremities of the patient 12 in general, and to the legs of the patient in particular. FIG. 10 shows that the thermal blanket has an overall shape that includes a primary portion having a relatively large, generally rectangular upper body portion 310 placed over the upper body of the patient 12 and a relatively narrow, elongated central lower body extension 312 having a width substantially less than the width of the upper body portion. In the preferred embodiment of FIGS. 10–12, the lower body extension 312 comprises a single inflatable tube of the type illustrated in FIGS. 3 and 4 that is used to cover at least one elongated member of the patient, such as a leg. Whereas the upper body portion comprises a plurality of inflatable tubes that are arranged transversely of the upper end of the lower body extension and are used to cover the chest area of the patient. The elongated central extension 312 and the transverse upperbody tubes 310 communicate internally so that a single inlet port 18 permits them to be simultaneously inflated.

FIG. 10 also shows that the lower end of the elongated lower body extension 312 is flanked by two gathered portions 314, 316. Each gathered portion includes an attachment flap 322 with an adhesive backing along its underside, as described previously for the other embodiments. Other attachment flaps can be provided at other blanket portions as desired, such as the attachment flaps 324 for securing edges of the upper body portion 310 to the patient 12. A head drape 326 also can be provided. FIG. 11 shows a first one 314 of the gathered portions in its deployed condition, while FIG. 12 shows the thermal blanket with both gathered portions in their respective deployed conditions, wherein full coverage of the patient is provided.

More particularly, FIG. 10 shows both of the gathered portions 314, 316 in their non-inflated condition and shows that they are coupled to the central extension 312 of the blanket 300 along the length of the central extension, on opposite sides. Each gathered portion 314, 316 has a closure 315, 317, respectively, that maintains the gathered portions in their non-inflated condition. FIG. 11 shows the blanket 300 after the closure 315 of the first gathered portion 314 has been opened, or removed, thereby permitting the inflating medium to enter the first gathered portion and inflate the first gathered portion so that it deploys transversely of the central extension 312. In FIG. 11, the closure 317 of the remaining second gathered portion 316 has not been removed and therefore that gathered portion remains in the non-inflated condition. FIG. 12 shows the blanket 300 after the closure 317 of the second gathered portion 316 also has been opened and after the second gathered portion has been inflated and deployed transversely of the central extension.

Figure 13:
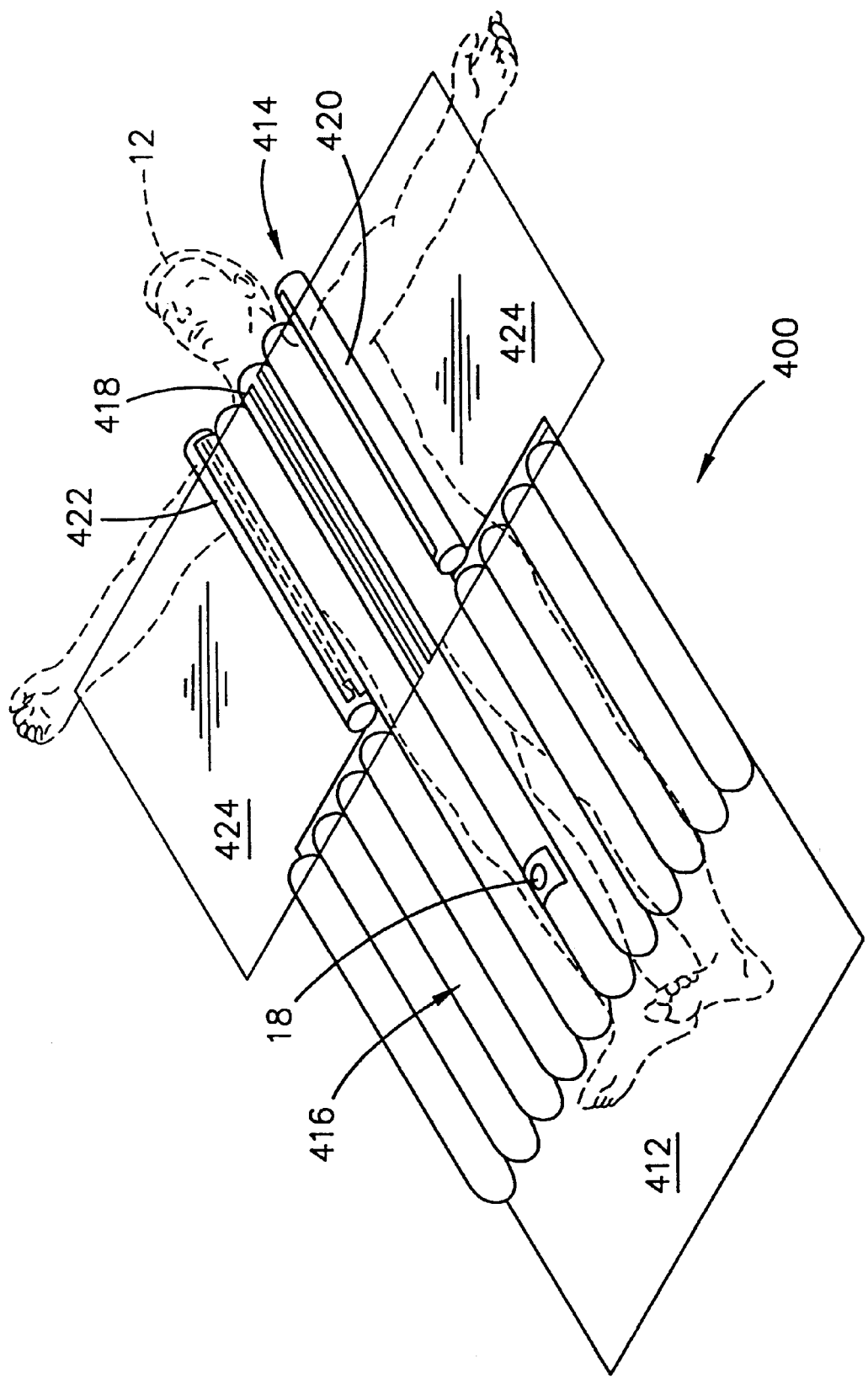
FIG. 13 and FIG. 14 are views of an inflatable thermal blanket constructed in accordance with the present invention to provide access to a patient's upper body during medical treatment.
Figure 14:
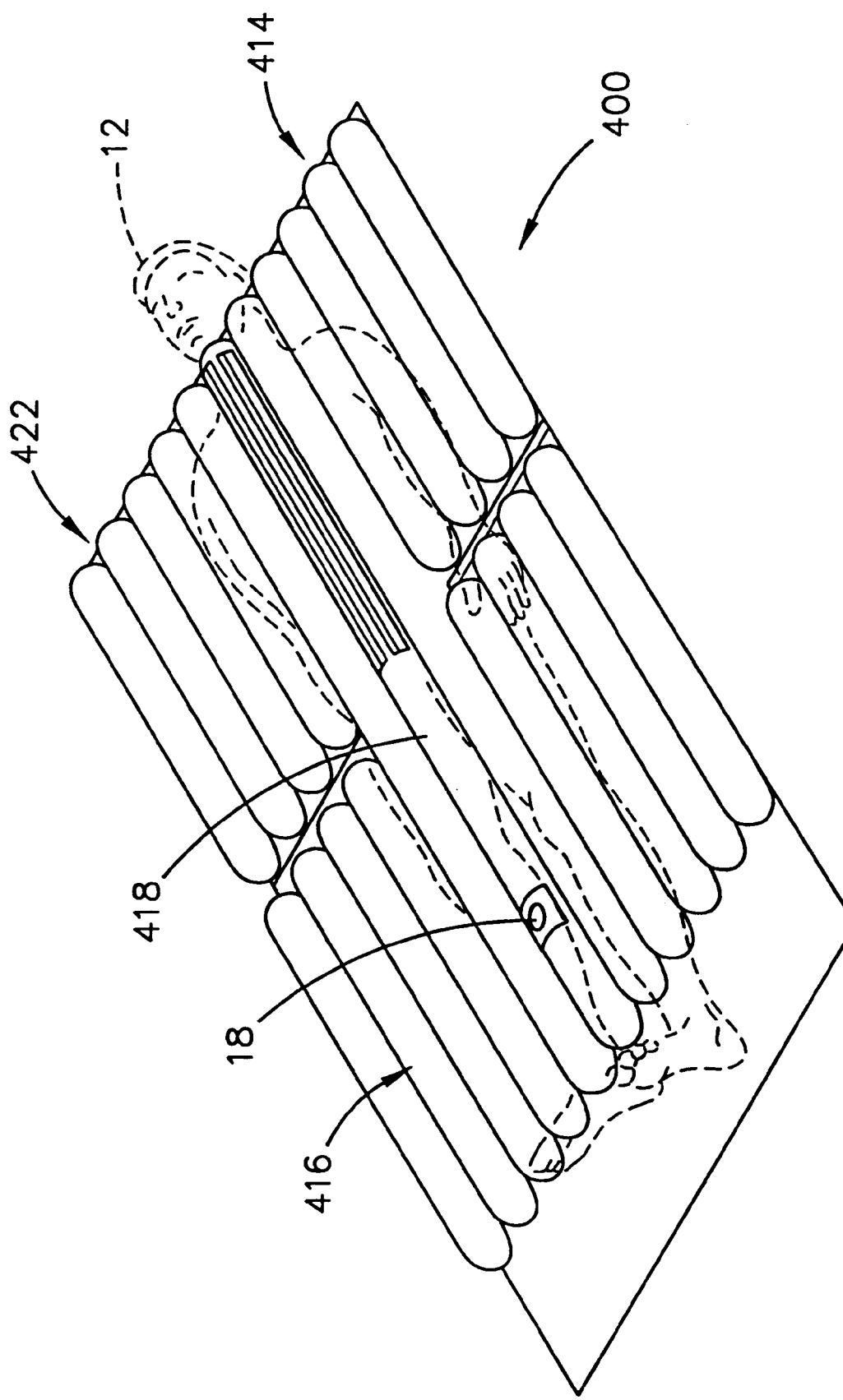

FIGS. 13 and 14 illustrate a blanket 400 similar to that shown in FIGS. 10–12, except that the blanket 400 leaves the arms of the patient 12 exposed and covers the lower extremities of the patient. Thus, the lower end 412 of the blanket covers the patient's lower extremities and the upper end 414 includes the gathered portions. Again, the primary portion of the blanket includes a relatively large portion 416 and a central extension 418 that is flanked by two gathered portions 420, 422. The gathered portions typically are deployed after medical care has been provided (FIG. 14) and it is desired to obtain full coverage of the patient. Lateral drapes 424 can be provided for supplemental coverage, if desired.

Figure 15:
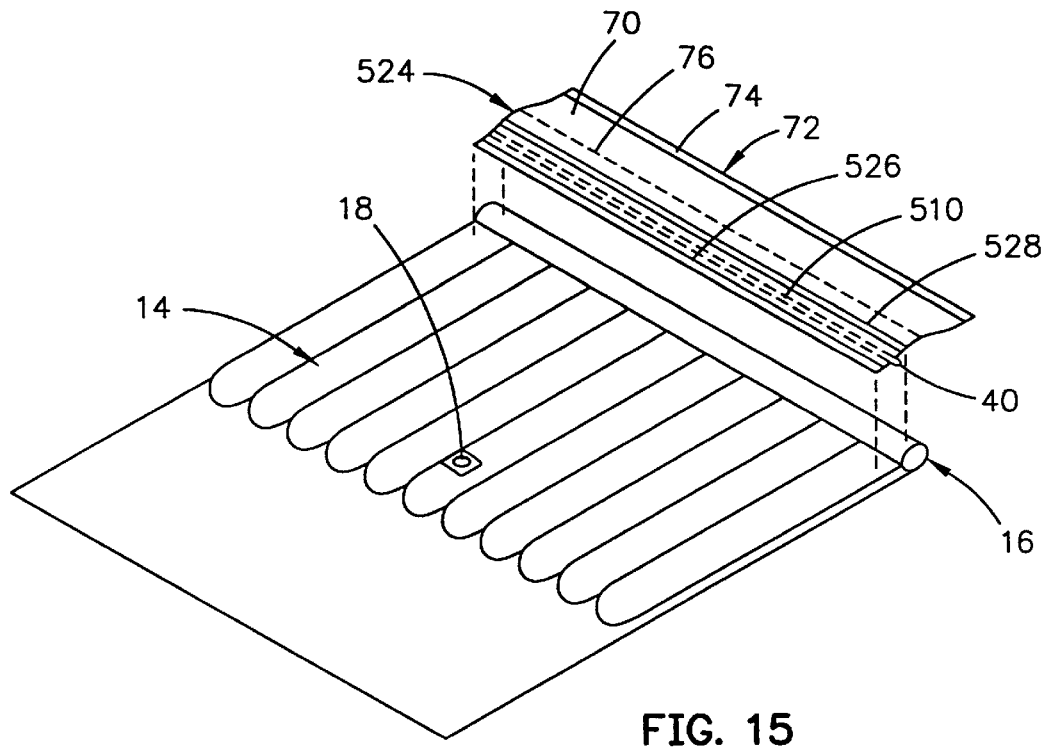
FIG. 15 and FIG. 16 are views of an inflatable thermal blanket constructed in accordance with the present invention having alternative closures to those illustrated in FIGS. 1–14.

The closure 24 of a thermal blanket constructed in accordance with the present invention can assume a variety of structures in addition to the pull strip described above. In FIG. 15, the closure comprises a tear string 510 that is embedded in the elongated strip 524 of the closure. Once again, the elongated closure strip includes a first edge 526 attached to the primary portion 14 of the blanket 10 and a second edge 528 attached to the gathered portion 16. The tear string includes an enlarged release tab 512 that can be grasped and pulled, tearing the string out from the elongated strip and thereby separating the edge of the elongated strip attached to the primary portion of the blanket from the edge of the elongated strip attached to the gathered portion. As before, an optional attachment flap 70 can be provided, having a free end 72 with an adhesive backing 74 applied to the underside and having a central perforation 76 for easy removal.

Figure 16:
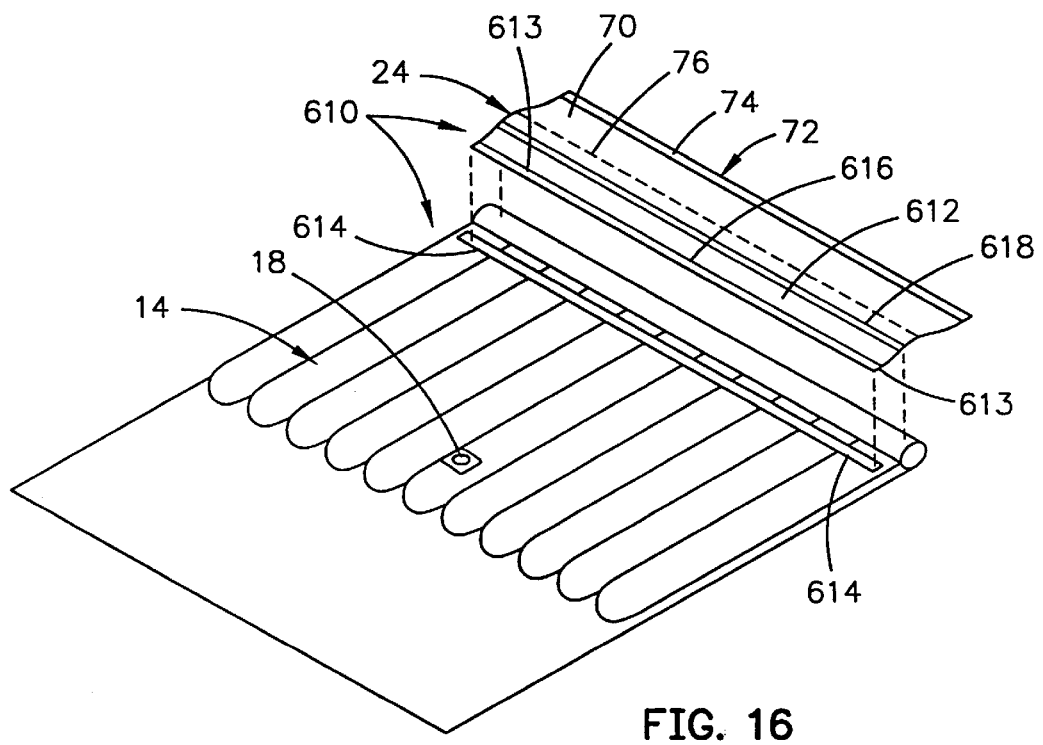

FIG. 16 shows a closure 24 comprising a hook and loop fastening system 610, such as commonly sold, for example, under the trademark "VELCRO." The hook and loop fastening system includes a hook strip 612 having loops or coils 613 of a plastic material and a loop strip 614 having a loose, or fuzzy, pile of material. The hook strip can be engaged with the loop strip and then released by forcibly pulling them apart. Although relatively modest forces will not separate the two strips, more deliberate pulling actions can be used to easily separate the hook strip from the loop strip. When engaged, the hook and loop fastening system provides a unitary strip that can be attached to the thermal blanket so as to maintain the gathered portion in the non-inflated condition.

In FIG. 16, the looped plastic material is attached to the underside of a first edge 616 of the hook strap, which then is attached to the gathered portion 16 along a second edge 618. Preferably, the attachment is by an adhesive backing. The loop strip 614 is attached to the primary portion 14 of the thermal blanket. It should be noted that the hook strip and loop strip can be mounted on the opposite blanket portions. To hold the gathered portion 16 in the non-inflated condition, the bottom of the first edge 616 is pressed into engagement with the loop strip 614. When it is desired to unfurl the gathered portion, the hook and loop fastening system is simply separated by pulling on the two respective strips in opposite directions. This releases the hook strip from the loop strip and permits the gathered portion to be unfurled, admitting the inflating medium into the gathered portion. As before, an attachment flap 70 can be included with the closure 610.

Thus, all of the embodiments described above provide an inflatable thermal blanket that can be used to permit access to a site of interest while controlling a patient's body temperature during surgery and then can be converted to a full-body covering that completely covers the patient.

The present invention has been described above in terms of presently preferred embodiments so that an understanding of the present invention can be conveyed. There are, however, many configurations for inflatable thermal blankets not specifically described herein but with which the present invention is applicable. For example, the closure can be provided by a light tackiness adhesive backing. The present invention should therefore not be seen as limited to the particular embodiments described herein, but rather, it should be understood that the present invention has wide applicability with respect to inflatable thermal blankets generally. All modifications, variations, or equivalent arrangements that are within the scope of the attached claims should therefore be considered to be within the scope of the invention.

I claim:

1. An inflatable thermal blanket, comprising:
    an inflatable covering with top and bottom surfaces;
    an inflation inlet in the inflatable covering;
    apertures opening through the bottom surface into the inflatable covering;
    a gathered portion of the inflatable covering maintained in a non-inflated condition adjacent a portion of the inflatable covering; and
    a releasable closure that maintains the gathered portion in the noninflated condition.

2. A thermal blanket as defined in claim 1, wherein the releasable closure includes a release element that releases the closure and permits the gathered portion to be inflated.

3. A thermal blanket as defined in claim 1, wherein the releasable closure includes a flap having a top surface and a bottom surface and an adhesive portion on the bottom surface.

4. A thermal blanket as defined in claim 3, wherein the flap includes a central perforation such that the central perforation can be broken.

5. A thermal blanket as defined in claim 1, wherein the gathered portion includes a substantially rectangular extension of the inflatable covering, the rectangular extension having top and bottom surfaces and communicating with the inflatable covering, along an attachment side such that the top and bottom surfaces of the rectangular extension are coextensive with the top and bottom surfaces, respectively, of the inflatable covering.

6. A thermal blanket as defined in claim 1, wherein the inflatable covering includes an uninflatable head end portion with a top edge, further including a removeable portion in the head end portion, adjacent the top edge.

7. An inflatable thermal blanket, comprising:
    an inflatable covering having top and bottom surfaces;
    an inflation inlet in the inflatable covering;
    apertures in the bottom surface from which an inflating medium can exit the inflatable covering; and
    a releasable closure that maintains a gathered portion of the inflatable covering in an uninflated, furled condition and prevents the inflating medium from entering the gathered portion, and permits the inflating medium to be admitted into the gathered unfurled portion, when released.

8. An inflatable thermal blanket as detinied in claim 7, wherein the releasable closure includes a release element that releases the closure and permits the gathered portion to be inflated.

9. An inflatable thermal blanket as defined in claim 7, further including attachment means for releasably attaching the gathered portion to a body.

10. A thermal blanket, comprising:
    an inflatable covering having opposed surfaces sealed along their edges to define an internal volume;
    an inflating inlet in the inflatable covering;
    apertures in a first surface of the inflatable covering,
    an inflatable extension covering coupled to the inflatable covering having opposed surfaces and an internal volume that communicates with the inflatable covering internal volume; and
    a releasable closure that maintains the extension covering in a non-inflated, furled condition such that the inflating medium is prevented from entering the internal volume of the extension covering and that can be opened to permit the inflating medium to be admitted into the internal volume of the extension covering such that the extension covering assumes an inflated, unfurled condition.

11. A thermal blanket as defined in claim 10, wherein the thermal blanket further includes an attachment flap having opposed surfaces and an adhesive portion on a first surface of said opposing surfaces.

12. A thermal blanket as defined in claim 11, wherein the attachment flap includes a central perforation that can be broken.

13. A method of covering and convectively controlling the temperature of a first area of a body and leaving a second area of the body exposed for rendering medical care to the exposed second area, the method comprising:
    placing an inflatable thermal blanket having an extension in a non-inflated, furled condition over the body such that a first portion of the thermal blanket covers the first area of the body and leaves the second area of the body exposed;

inflating the first portion of the inflatable thermal blanket;

releasing a closure of the inflatable thermal blanket such that the extension of the inflatable thermal blanket is changed from the non-inflated, furled condition in which the inflating, medium is prevented from entering the extension to an inflated, unfurled condition in which the inflating medium is admitted into the extension and the inflated extension covers the second area of the body.

14. A method as defined in claim 13, wherein releasing includes opening a closure that includes an elongated strip attached along a first edge to the first portion of the inflatable thermal blanket and attached along a second edge to the extension of the inflatable thermal blanket.

15. A method as defined in claim 14, wherein opening a closure includes tearing the elongated strip along at least one central perforation that extends along the length of the elongated strip.

16. A method as defined in claim 14, wherein opening a closure includes pulling a tear string embedded in the elongated strip so as to separate the first longitudinal edge of the elongated strip from the second longitudinal edge of the elongated strip.

17. A method as defined in claim 14, wherein opening a closure includes pulling apart a releasably interlocked hook strip attached to one of the primary portion of the thermal blanket or the extension from a loop strip attached to the other of the primary portion or the extension.

18. A method as defined in claim 13, wherein placing includes attaching an attachment flap that extends outwardly from the first portion of the thermal blanket to the body.

19. A method as defined in claim 13, further including releasing the attachment flap of the first portion from the body and moving the thermal blanket to a new position relative to the body.

20. A method as defined in claim 19, wherein releasing the attachment flap includes separating a first half of an elongated strip from a second half of the elongated strip wherein the first half is attached along a longitudinal edge to the first portion of the thermal blanket and the second half is attached along a longitudinal edge to the body.

21. A method as defined in claim 20, wherein separating includes tearing the elongated strip along at least one central perforation that extends along the length of the elongated strip.

22. A method as defined in claim 19, wherein the thermal blanket includes an inflatable, removable head end portion, the method further including, prior to moving, removing the removable portion and rotating the thermal blanket with respect to the body, the new position including a position in which the head of the body is received in a recess formed in the head end portion by removal of the removable position.

* * * * *

UNITED STATES PATENT AND TRADEMARK OFFICE
CERTIFICATE OF CORRECTION

PATENT NO. : 5,964,792
DATED : October 12, 1999
INVENTOR(S) : Augustine

It is certified that error appears in the above-identified patent and that said Letters Patent is hereby corrected as shown below:

Column 8, line 27, change "detinied" to --defined--.

Signed and Sealed this

Twenty-eighth Day of March, 2000

Attest:

Q. TODD DICKINSON

*Attesting Officer*   *Commissioner of Patents and Trademarks*

UNITED STATES PATENT AND TRADEMARK OFFICE
CERTIFICATE OF CORRECTION

PATENT NO.    : 5,964,792
DATED         : October 12, 1999
INVENTOR(S)   : Scott D. Augustine It is certified that error appears in the above-identified patent and that said Letters Patent is hereby corrected as shown below:

<u>Title page,</u>
Item [63], please add after "5,733,318" -- , which is a continuation of application No. 08/315,960, filed on Sep. 30, 1994, now U.S. Patent No. 5,545,194 --.

<u>Column 1,</u>
Line 5, please add after "5,733,318" -- , which is a continuation of application No. 08/315,960, filed on Sep. 30, 1994, now U.S. Patent No. 5,545,194 --.

Signed and Sealed this

Fourth Day of March, 2003

*Attest:*

JAMES E. ROGAN
*Attesting Officer*          *Director of the United States Patent and Trademark Office*